(12) United States Patent
Pennemann et al.

(10) Patent No.: US 7,307,190 B2
(45) Date of Patent: *Dec. 11, 2007

(54) PROCESS FOR THE PREPARATION OF TOLUENEDIAMINE

(75) Inventors: Bernd Pennemann, Bergisch Gladbach (DE); Bill Brady, Houston, TX (US); Rainer Buse, Cologne (DE); Gerd Greger, Kempen (DE)

(73) Assignee: Bayer MaterialScience AG, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/482,404

(22) Filed: Jul. 7, 2006

(65) Prior Publication Data

US 2007/0015940 A1    Jan. 18, 2007

(30) Foreign Application Priority Data

Jul. 12, 2005   (DE) ............... 10 2005 032 430

(51) Int. Cl.
*C07C 209/00*   (2006.01)
*C07C 249/00*   (2006.01)

(52) U.S. Cl. .................... 564/347; 560/360

(58) Field of Classification Search ........... 564/347
See application file for complete search history.

(56) References Cited

U.S. PATENT DOCUMENTS

| | | | |
|---|---|---|---|
| 2,471,134 A | 5/1949 | Wright | 196/100 |
| 3,420,752 A | 1/1969 | Kirss et al. | 203/94 |
| 4,720,326 A | 1/1988 | Beckhaus et al. | 203/14 |
| 5,849,947 A | 12/1998 | Biskup et al. | 560/347 |
| 6,359,177 B1 | 3/2002 | Brady et al. | 564/424 |
| 6,547,933 B2 | 4/2003 | Marion et al. | 203/78 |
| 7,108,770 B2 * | 9/2006 | Grun et al. | 203/29 |
| 7,118,653 B2 * | 10/2006 | Brady et al. | 203/29 |

FOREIGN PATENT DOCUMENTS

WO    2005/066113 A1    7/2005

OTHER PUBLICATIONS

Ing. Eng. Chem. Res. 37, (month unavailable) 1998, pp. 3444-3454, Rakesh Agrawal and Zbigniew T. Fidkowski, "Are Thermally Coupled Distillation Columns Always Thermodynamically More Efficient for Ternary Distillations."

* cited by examiner

*Primary Examiner*—Samuel Barts
(74) *Attorney, Agent, or Firm*—Lyndanne M. Whalen

(57) ABSTRACT

Toluenediamine is produced and separated from by-products of the reaction by:
a) hydrogenating dinitrotoluene in the presence of a catalyst,
b) separating the catalyst, water and optionally solvent from the hydrogenation reaction mixture to give crude toluenediamine, and
c) separating by distillation the crude toluenediamine in a separating wall column into at least four product streams P1, P2, P3 and P4. The product stream P1 is a stream containing low boilers. The product stream P2 is a stream containing o-toluenediamine. The product stream P3 is a stream containing m-toluenediamine. The product stream P4 is a stream containing high boilers and m-toluenediamine.

14 Claims, 5 Drawing Sheets

PROCESS FOR THE PREPARATION OF TOLUENEDIAMINE

BACKGROUND OF THE INVENTION

This invention relates to a process for the preparation of toluenediamine (TDA) and its separation into desired and undesired components. In this process, dinitrotoluene is hydrogenated and any solvent present, as well as water and other by-products, are separated from the resulting reaction mixture by distillation. A separating wall column is used for the subsequent separation of the dewatered mixture into desired isomers and undesired isomers, by-products that are still present, and high-boiling compounds.

According to the state of the art, m-TDA (a 2,4- and 2,6-isomer mixture) is prepared by the hydrogenation of dinitrotoluene for use in the preparation of TDI by phosgenation. The hydrogenation can take place in the presence of solvents. The catalyst is conventionally separated off first. This can be carried out, e.g., by filtration or sedimentation. In addition to the TDA target product and water by-product, organic by-products are also formed in the hydrogenation. These include low boilers and high boilers. Low boilers are compounds whose boiling point is below that of TDA. High boilers are compounds having a higher boiling point than the TDA target product.

These by-products can severely interfere with the use of the TDA target product in applications, especially the preparation of toluene diisocyanate (TDI by phosgenation. It is therefore necessary to separate the reaction mixture obtained into its components.

If solvent is added in the hydrogenation reaction, it is separated off first. This is generally effected in known manner by distillation in a continuous distillation column, the solvent being recovered by a suitable procedure in a sufficiently pure state to be able to be used directly in the process without further purification. It is also possible to separate the solvent from the reaction product by distillation, together with some or all of the water formed, and then to recover the solvent in the required purity in another process stage. If the reaction is carried out without the addition of solvent, this solvent separation is of course unnecessary.

This is then conventionally followed by drying of the TDA, i.e. the removal of the water of reaction, which makes up approx. 40 wt. % of the reaction mixture obtained. In principle, this can be done by simply stripping the water off by heating the TDA solution under vacuum and driving the vapors off. However, in this simple procedure, the water separated off is not obtained in the purity required for problem-free disposal, but is always contaminated with TDA. The water of reaction is therefore better removed by distillation in a suitable distillation apparatus. This is done, e.g., by heating the crude TDA solution in a column to a temperature of 200° C., the water being obtained at the top in pure form if the column is operated at normal pressure or a slight excess pressure and has about 20 to 30 trays. The TDA is then withdrawn from the bottom and the last traces of water are removed by expansion into a vacuum of 30 to 300 mbar.

A variant of this process is described in EP-A-0 236 839. This disclosed process allows water and highly volatile compounds, and to some extent also low boilers, to be separated off.

The mixture obtained (crude TDA) conventionally is generally composed of m-TDA containing less than 10 wt. % of ortho isomers, less than 5 wt. % of high boilers, less than 5 wt. % of low boilers and less than 5 wt. % of water.

Separation of the 2,3- and 3,4-isomers from the TDA isomer mixture is known. Thus, for example, U.S. Pat. No. 3,420,752 discloses the use of a distillation column for this separation, o-TDA being obtained at the top and m-TDA at the bottom. As the crude TDA obtained from the reaction normally contains low boilers and high boilers, it is immediately clear that, without further measures, the top product contains not only o-TDA but also low boilers. Likewise, the bottom product will contain not only m-TDA but also high boilers. In the case of m-TDA, these impurities constitute a disadvantage of this process because these high boilers are undesired in the target product, so they have to be separated off before further use of the m-TDA for example, in the preparation of TDI by phosgenation.

U.S. Pat. No. 6,547,933 describes a process in which m-TDA is obtained free of high boilers. In one embodiment of this process, the crude TDA is separated into its isomers in a distillation column. A partial stream is withdrawn as vapor from the bottom third of the distillation column and transferred to a condenser to give m-TDA free of high boilers. However, an appreciable part of the product stream is still made up of m-TDA containing high boilers, which are then used, e.g., in a downstream phosgenation. In another variant of the process, an m-TDA stream is withdrawn from the column and partially evaporated. The resulting vapor stream is condensed to give m-TDA free of high boilers. The unevaporated portion, which contains high boilers, is recycled into the column. Another m-TDA stream, again containing high boilers, is withdrawn from the bottom of the column. In both variants, the stream containing high boilers that is discharged from the bottom will contain a substantial part of the m-TDA produced. Thus the process can only be employed economically if this stream containing high boilers is utilized. The object of the present invention is therefore not achieved in this disclosed process.

The process disclosed in U.S. Pat. No. 6,359,177 achieves a complete separation of the high boilers from the m-TDA. This is done by first separating the TDA into its isomers in a distillation column. The mixture of m-TDA and high boilers obtained as the bottom product is separated into an m-TDA stream and a high boiler stream in a second apparatus, which is made up of an evaporator and a condenser. The m-TDA still contained in the high boiler stream is depleted in another stripping column and partially replaced with o-TDA. This gives a stream containing essentially high boilers and o-TDA, which is discharged and, e.g., incinerated. A second stream, composed of o-TDA and m-TDA, is recycled into the isomer distillation column. Variants of this process are also described in U.S. Pat. No. 6,359,177. This process achieves the object of minimizing the m-TDA losses in the high boiler stream to be discharged, but it entails increased equipment and energy costs.

In thermal separation technology, it is often desired to separate a multi-component mixture into its individual components. In the case of one inflow and two product streams, it is possible to use the top and bottom outflows of a distillation column. In the case of multi-component mixtures, a further split can be achieved by repeating the separation into two streams. The disadvantage is that this procedure requires additional equipment such as columns, condensers or evaporators. This in turn increases the operating energy requirements and the associated costs. Numerous publications address the problem of reducing the equipment and energy costs involved in separating a mixture of substances, the yardstick for the energy efficiency of a separation sequence being the Petlyuk system (cf., for example, R. Agrawal, Z. Fidowski, "Are thermally coupled distillation columns always thermodynamically more efficient for ternary distillations?", Ind. Eng. Chem. Res., 1998, 37, pp. 3444-3454). In this configuration, a preliminary separation column separates the inflow into two streams using the split vapor stream of the stripping section of the main column and the split liquid outflow of the rectifying section of the main column. The resulting vapor and liquid streams leaving the preliminary separation column are enriched in low or high boilers. These two streams are introduced into the main column. This configuration offers advantages in terms of the purity of the product withdrawn as a side stream. On the other hand, the purity of the inflows into the stripping and rectifying sections of the main column is improved by this arrangement. A high purity of the three product streams is achieved in this way.

U.S. Pat. No. 2,471,134 discloses an improvement to this procedure in which the preliminary separation column and main column are combined in one apparatus that is divided in the middle by a separating wall. This column is equipped with an evaporator and a condenser. The column is then made up of 4 segments. These are a common rectifying section at the top of the column, a common stripping section at the bottom of the column, and a preliminary separation segment and a main segment that are located next to one another in the middle section of the column and are separated by a wall. The mixture is introduced onto or into the preliminary separation segment, the top product is drawn off above the common rectifying section and the bottom product is drawn off below the common stripping section. The intermediate-boiling product is withdrawn from the main segment as a side stream. This separating wall column offers advantages in terms of the hydraulics of the whole system and reduces the equipment costs of the Petlyuk process.

SUMMARY OF THE INVENTION

The object of the present invention is to provide a simple and economic process for the preparation of toluenediamine and its separation into m-TDA, o-TDA, low boilers and high boilers in which (1) the m-TDA contained in the crude TDA is freed of o-TDA, low boilers and high boilers and (2) at the same time, the m-TDA losses, the equipment costs and the energy requirements of the process are kept small.

This and other objects which will be apparent to those skilled in the art are achieved by using a separating wall column in the process according to the invention.

DETAILED DESCRIPTION OF THE INVENTION

Figure 1:
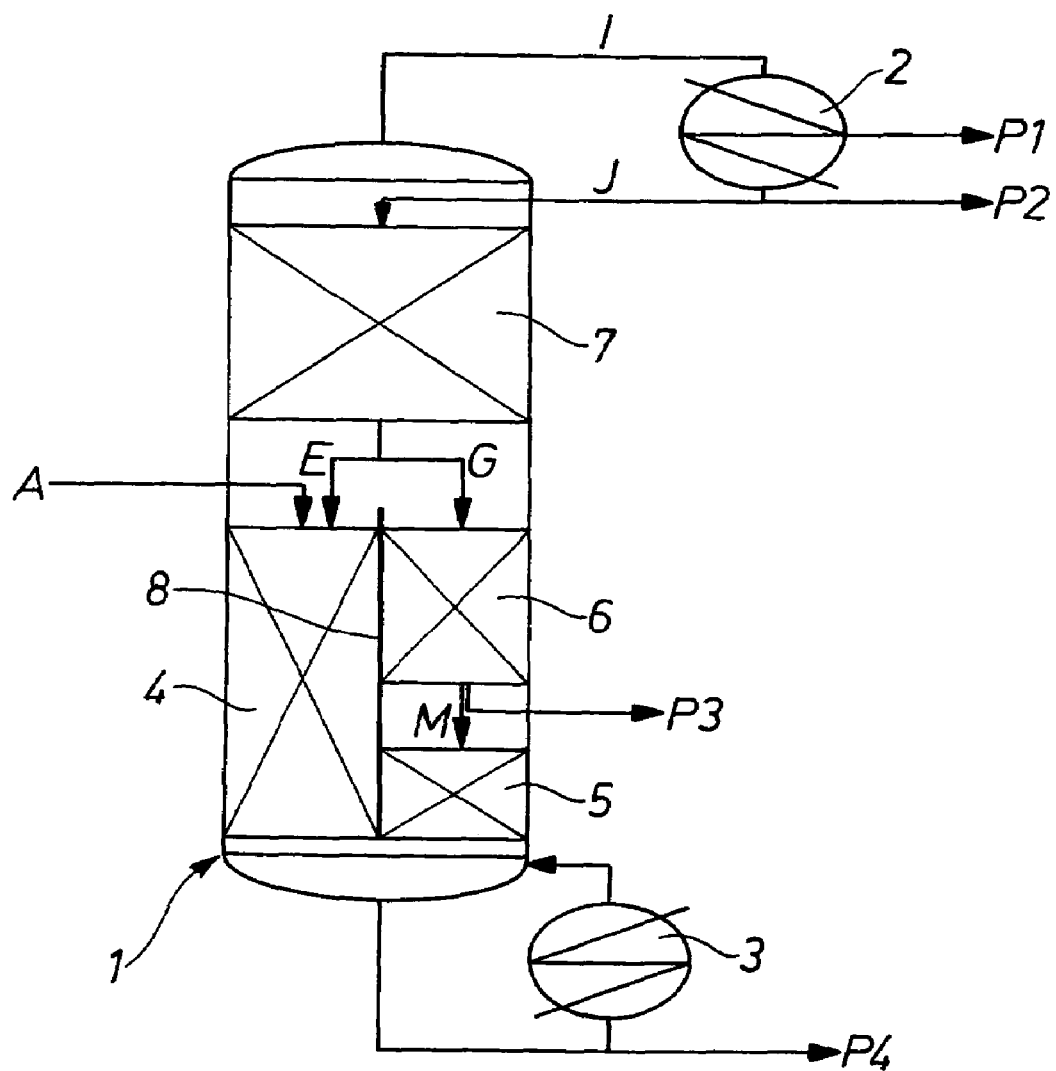
FIG. 1 is a schematic diagram of a separating wall column suitable for use in the process of the present invention.
Figure 2:
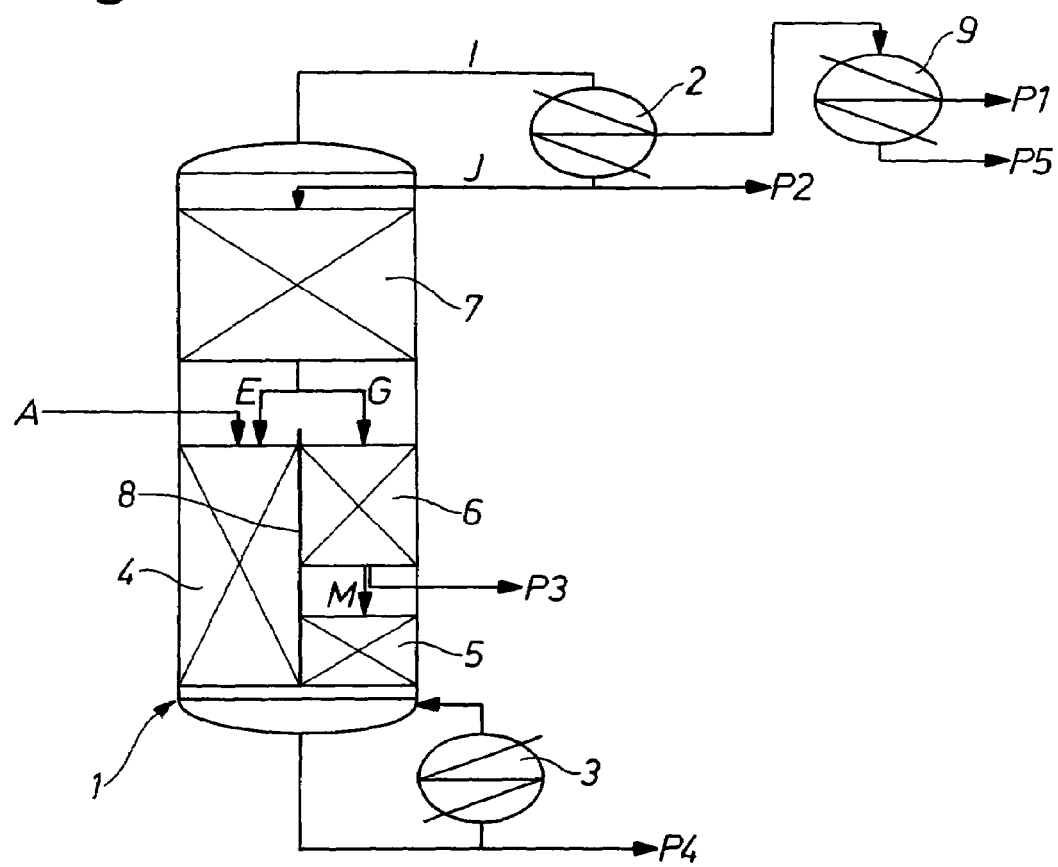
FIG. 2 illustrates an embodiment of the process of the present invention in which an additional condenser is used. In this embodiment, P5 is a stream enriched in low boilers, compared with the vapor stream I from column 1, while P2 is a stream depleted in low boilers.

The invention relates to a process for the preparation of m-TDA in which:

a) dinitrotoluene is hydrogenated in the presence of a catalyst, after which the catalyst, water and optionally solvent are separated off to give crude toluenediamine, and b) the crude toluenediamine is separated by distillation in a separating wall column to give at least four product streams P1, P2, P3 and P4, where the product stream P1 is a stream containing low boilers, the product stream P2 is a stream containing o-TDA,
the product stream P3 is a stream containing m-TDA, and
the product stream P4 is a stream containing high boilers and m-TDA.

The term m-TDA encompasses the isomers 2,4-TDA and 2,6-TDA. The term o-TDA correspondingly encompasses the isomers 2,3-TDA and 3,4-TDA.

FIGS. 1 to 5 show variants of separating wall columns that can be used in the process according to the invention.

The inflow of the separating wall column (inflow A in FIGS. 1-5) contains preferably at least 75 wt. %, more preferably at least 87 wt. % and most preferably at least 93 wt. % of m-TDA and preferably also contains less than 10 wt. % of o-TDA, less than 5 wt. % of high boilers, less than 5 wt. % of low boilers and less than 5 wt. % of water. More preferably, the inflow contains, in addition to the m-TDA, less than 3 wt. % of high boilers, less than 2 wt. % of low boilers, less than 2 wt. % of water and less than 6 wt. % of o-TDA. Most preferably, the inflow contains, in addition to the m-TDA, less than 2 wt. % of high boilers, less than 1 wt. % of low boilers, less than 1 wt. % of water and between 2 and 5 wt. % of o-TDA.

The product stream P1 is a vapor stream containing low boilers and preferably inert substances, water, low boilers and o-TDA. Examples of inert substances are nitrogen and air. Examples of low boilers are toluidines and diaminomethylcyclohexane. The o-TDA content of this stream is preferably less than 75 wt. % and more preferably less than 50 wt. %, the amount of water corresponding essentially to the amount in the inflow A and the rest of the stream being essentially low boilers. This stream preferably contains less than 30 wt. % of water. In order not to burden a downstream vacuum production unnecessarily, this stream can be subjected to a post-condensation so that the low boilers, in particular, can be collected and disposed of.

The product stream P2 preferably contains predominantly o-TDA and can also contain low boilers and m-TDA, the m-TDA content being adjustable within wide limits. In practice, however, 20 wt. % of m-TDA will rarely be exceeded without a compelling reason. The m-TDA concentrations are preferably below 10 wt. % and more preferably below 5 wt. %. Whether the streams P1 and P2 are obtained together or have to be separated depends on the intended use of the o-TDA. How this separation is effected, if appropriate, depends on the composition of the inflow and the required purity of the o-TDA. If a separation is necessary, the proportion of low boilers which one will normally want to obtain in practice is less than 5 wt. %, preferably less than 3 wt. % and more preferably less than 1 wt. %. The o-TDA content is preferably greater than 90 wt. % and more preferably greater than 97 wt. %.

The product stream P3 preferably contains predominantly m-TDA. The o-TDA content can be adjusted as a function of the number of theoretical plates in the separating wall column and/or of the reflux ratio. The o-TDA contents are preferably below 2 wt. %, more preferably below 1 wt. % and most preferably below 0.5 wt. %. The content of high boilers is preferably less than 0.5 wt. % and more preferably less than 0.3 wt. %. The m-TDA content is preferably more than 97 wt. %, more preferably greater than 98.5 wt. % and most preferably greater than 99.5 wt. %.

The product stream P4 is a stream containing high boilers and m-TDA. The m-TDA content of the product stream P4 is preferably from 20 to 80 wt. % and more preferably from 30-70 wt. %. The content of high boilers is preferably greater than 20 wt. %, more preferably greater than 30 wt. % and most preferably greater than 40 wt. %, but less than 80 wt. %.

The product stream P4 is preferably treated further in order to recover the m-TDA it contains.

The invention is described in greater detail with reference to FIGS. 1-5.

FIG. 1 is a schematic diagram of a separating wall column 1 suitable for use in the process of the present invention. A represents the inflow ("crude TDA"). The product stream P1 is the stream containing low boilers, the product stream P2 is the stream containing o-TDA, the product stream P3 is the stream containing m-TDA and the product stream P4 is the stream containing high boilers and m-TDA. The separating wall column 1 is provided with a condenser 2, an evaporator 3, a separating wall 8 and separating segments 4, 5, 6 and 7. The inflow A is preferably introduced from above into the separating segment 4, the upper edge of which is substantially level with the upper edge of the separating wall 8. However, the upper edge of the separating segment 4 can also be below the upper edge of the separating wall 8. The separating segment 4 is used for the preliminary separation of the inflow A and the separating segment 5 is used for the separation of high boilers and m-TDA. An additional separating segment can also be provided below the separating wall. The liquid stream exiting the segment 7 is split: the stream E is introduced into the segment 4 and the stream G into the segment 6 located on the opposite side of the separating wall 8. The liquid stream exiting the segment 6 is split: part of it is introduced as the stream M into the segment 5 located below it, and the rest is discharged as the product P3.

Conventionally, the crude TDA (stream A) is introduced on one side of the separating wall, the stream P3 containing m-TDA is withdrawn on the other side of the separating wall and the stream P4 containing high boilers and m-TDA is withdrawn below the separating wall. In one variant of the process according to the invention, the vapor stream I obtained at the top of the column, which contains essentially o-TDA and low boilers, is condensed and part of it is introduced into the column as the reflux J. The liquid stream not required for the reflux is withdrawn as the stream P2 containing o-TDA, and utilized further.

The number of separating stages needed depends on the required purities of the product streams and can be determined in a manner known to those skilled in the art. The segments 4 and 6 have preferably at least 8 theoretical plates and more preferably between 10 and 30. The segment 7 has preferably at least 13 theoretical plates and more preferably between 15 and 40. If a one-stage separation of m-TDA and high boilers is sufficient to maintain the desired composition of the product stream P4, the segment 5 and the stream M can be omitted. The segment 5 preferably has fewer than 10 theoretical plates.

In another variant of the process according to the invention, if the stream P2 containing o-TDA is required to have a higher purity, initially only part of the vapor stream I obtained at the top of the column (containing essentially o-TDA and low boilers) can be condensed in the condenser 2. This part of the vapor stream I conventionally represents only 50 to 90 wt. % of the condensable compounds. This embodiment is shown by way of example in FIG. 2. The resulting condensate (stream P2) has a higher o-TDA content than the vapor stream I. This yields a purer o-TDA, of which part is then used as reflux and part is discharged as the product stream P2. The proportion condensed in the condenser 2 depends on the content of o-TDA and low boilers in the inflow and on the required amount and purity of the o-TDA stream P2. The still uncondensed vapors are conventionally post-condensed in a one-stage or multistage condenser 9. The resulting condensates (P5 in FIG. 2 and optionally other condensates) have increasingly high contents of low boilers and are therefore conventionally collected separately and utilized further. The design of the number of condensers and the particular condensation efficiency depends essentially on the required purity of the o-TDA and low boiler streams. Using this information, those skilled in the art will easily be able to choose the most favorable variant. In this embodiment, P5 is a stream enriched in low boilers, compared with the vapor stream I from the separating wall column 1, while P2 is a stream depleted in low boilers. The stream P5 preferably contains less than 70 wt. % of o-TDA, the rest being primarily low boilers and water.

Figure 3:
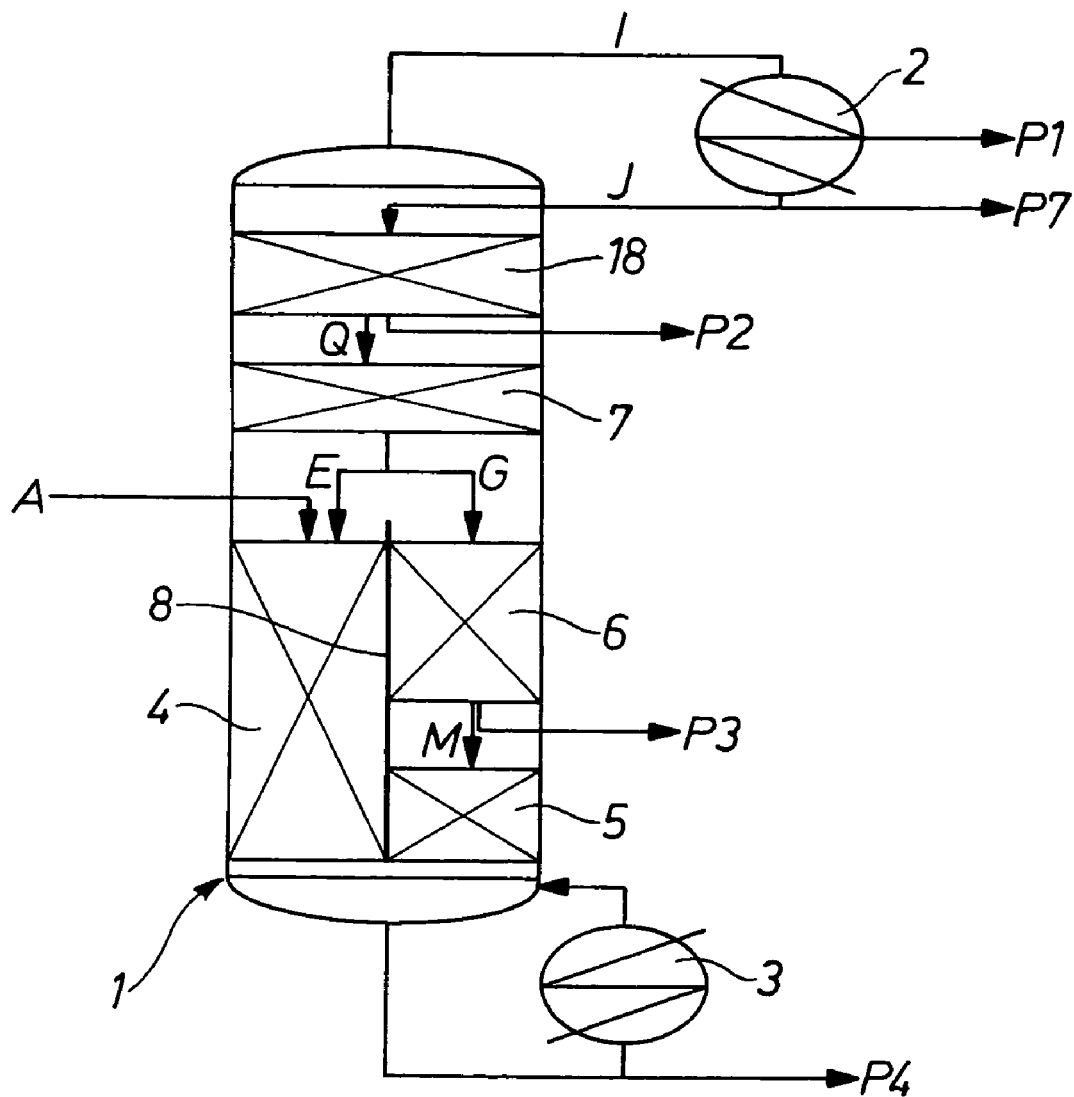
FIG. 3 illustrates another embodiment of the process of the present invention. In this variant, the product stream P2 containing o-TDA is obtained in high purity by withdrawal from the separating wall column as a side stream.

Another preferred embodiment of the process according to the invention likewise leads to higher purities of the product stream P2 with respect to o-TDA, coupled with a reduction in the proportion of o-TDA present in the product stream P1 containing low boilers. Here, as shown in FIG. 3, the distillation column is provided with a side take-off at which the product stream P2 containing o-TDA is withdrawn. The separating segment 18 located above the side take-off is designed so that the desired content of low boilers can be achieved in the product stream P2 containing o-TDA. The stream Q is the reflux for the segment 7. The content of low boilers in the stream P2 will be adjusted preferably to less than 3 wt. % and more preferably to less than 1 wt. %. In this embodiment, the vapor stream I is condensed in the condenser 2 and part of the condensate is introduced into the column as the reflux J and part is discharged as the stream P7. The number of separating stages in the segment 18 depends on the required purity of the product stream P2. The segment 18 has preferably between 1 and 20 theoretical plates and more preferably between 2 and 10.

In another embodiment of the process according to the invention, m-TDA can be separated in another process step from the product stream P4 containing high boilers and m-TDA. To do this, the product stream P4 containing high boilers and m-TDA is withdrawn from the bottom of the separating wall column 1 and m-TDA is then separated off in an additional apparatus. This can be effected in different ways.

Figure 4:
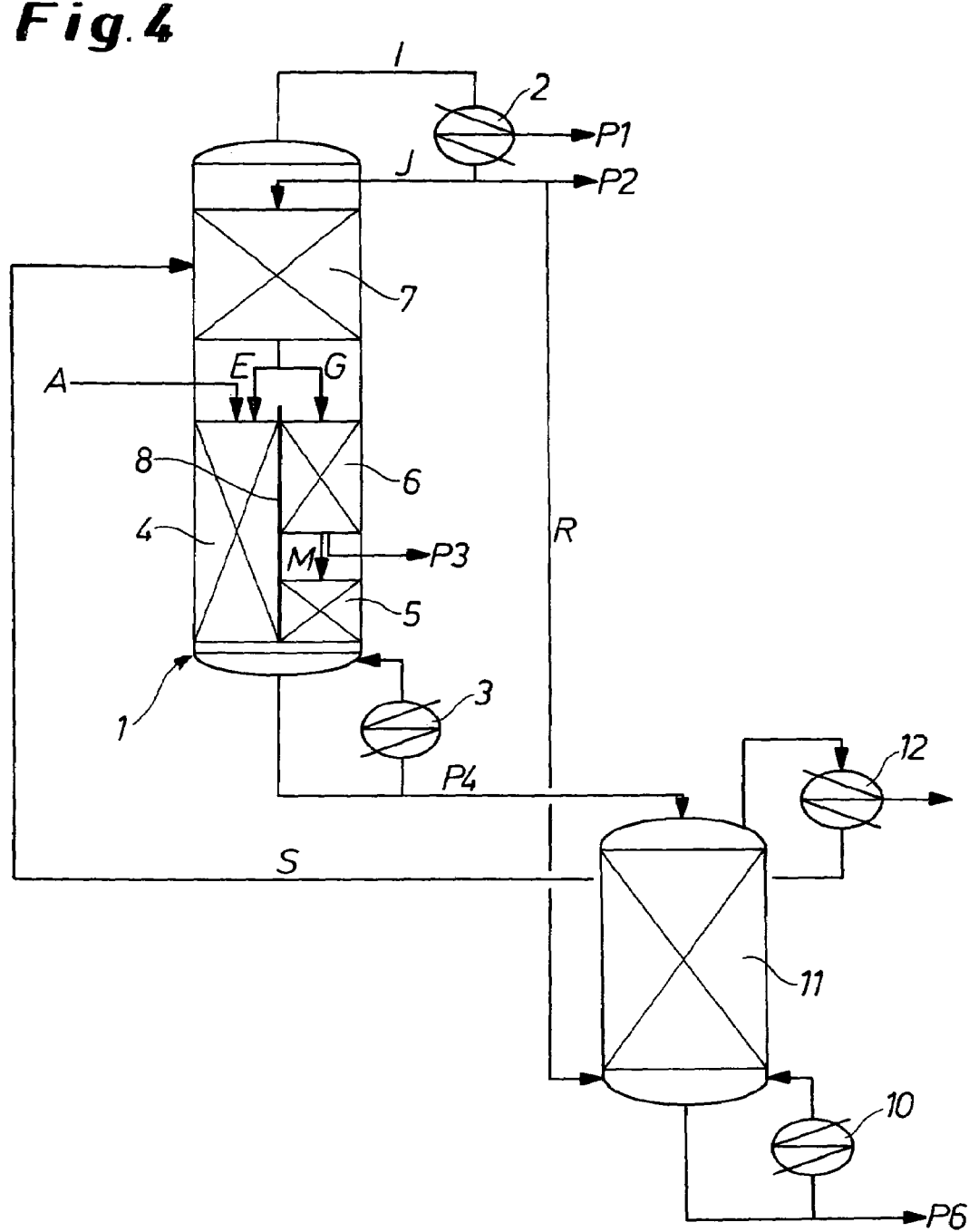
FIG. 4 illustrates an alternative embodiment of the process of the present invention in which the stream P4 containing high boilers and m-TDA is depleted in m-TDA in another process step.

The isolation of the m-TDA contained in the product stream P4 and its separation from the high boilers can be carried out as described in EP-A-0 794 170 or U.S. Pat. No. 6,359,177. This is done in accordance with the present invention by combining the distillation of the crude TDA in the separating wall column 1 with recovery of the m-TDA contained in the mixture of high boilers and m-TDA. FIG. 4 shows an example of a preferred embodiment of this novel combination using the technology disclosed in U.S. Pat. No. 6,359,177. The stream P4 is subjected to a further process step, which is carried out in a system comprising a distillation column 11, an evaporator 10 and a condenser 12. The liquid stream P4 is introduced into the top of the distillation column 11. The whole of the stream P2 or part of it (stream R) is introduced into the distillation column 11 below the inflow of the stream P4, for example into the bottom of the column or, e.g., via the evaporator 10 hydraulically connected to the bottom of the distillation column 11. A stream P6 containing high boilers, o-TDA and m-TDA is drawn off from the bottom of the distillation column 11 or, e.g., via the evaporator 10 hydraulically connected to the bottom of the distillation column 11. However, the major part of the m-TDA present in the inflow P4 is obtained as a mixture with the residual o-TDA as the stream S. The stream S is recycled into the separating wall column 1 for further separation. This procedure reduces the amount of m-TDA discharged together with the high boilers and thereby further increases the yield of the process. Preferably, the stream P6 contains between 20 and 80 wt. % of high boilers and the rest is composed essentially of o-TDA and m-TDA, o-TDA preferably being predominant. More preferably, the stream P6 contains between 30 and 70 wt. % of high boilers and less than 10 wt. % of m-TDA, the rest being essentially o-TDA.

In a similarly preferred variant of this process, the product stream P4 discharged from the bottom of the separating wall column 1, which contains high-boilers and m-TDA, will be processed further in order further to reduce the m-TDA losses. A kneader dryer, for example, can be used for this purpose. This is operated in a vacuum under the action of heat, evaporating the m-TDA contained in the inflow of the kneader dryer. The resulting vapor stream is introduced, e.g., into a condenser and the m-TDA obtained is recycled into the process or can be mixed with the product stream P3. In another variant of the process according to the invention, the vapor stream can be recycled directly into the separating wall column 1. To reduce the viscosity of the high boiler obtained, the latter can be mixed with a suitable low-viscosity liquid. This is preferably done using, if available, all or part of a stream containing low boilers (e.g., the stream P5 in FIG. 2) and/or all or part of the product stream P2 containing o-TDA.

Figure 5:
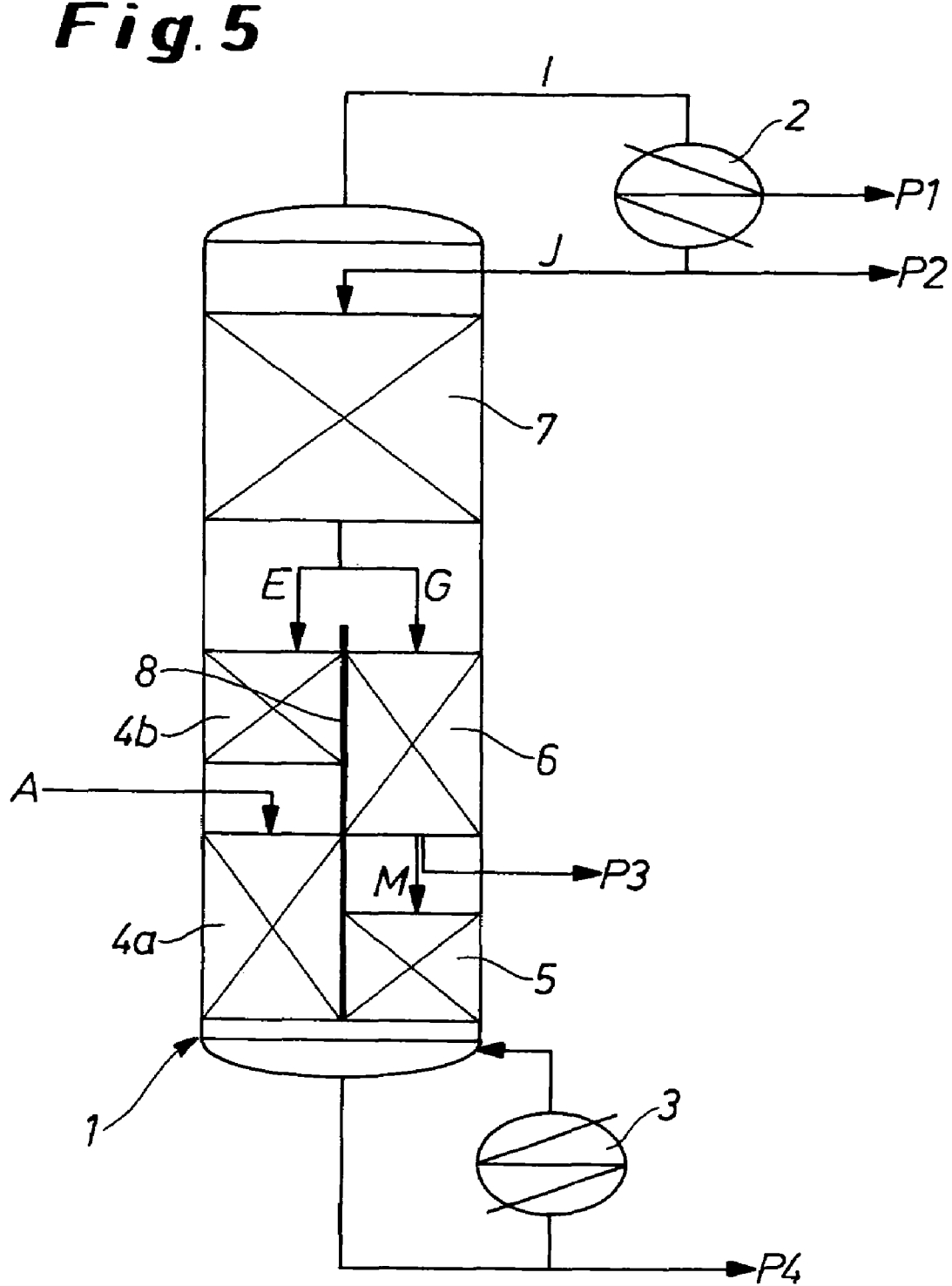
FIG. 5 shows another embodiment of the process of the present invention in which the separating segment for preliminary separation of the inflow is subdivided into two partial segments arranged one above the other, and the inflow is introduced into the separating wall column between the two partial segments.

In another embodiment of the process according to the invention, the separating segment for preliminary separation of the inflow A is subdivided into an upper partial separating segment 4b and a lower partial separating segment 4a located below it. This preferred embodiment is shown in FIG. 5. The inflow A is introduced into the separating wall column 1 between the upper partial separating segment 4b and the lower partial separating segment 4a. This arrangement is particularly advantageous if the column inflow A contains high boilers that boil only a little above m-TDA. In this case, the segment 4b serves to separate these high boilers from the inflow, thereby reducing the content of these high boilers in the refluxes E and G and hence also in the product stream P3. The extent of the energy saving is substantially dependent on the o-TDA content of the inflow, the required o-TDA content of the product P3, the number of theoretical separating plates in the segment 5 that are required to separate off the high boilers, and the reflux M required in the segment 5. The variant must therefore be chosen and designed for each individual case. The crude TDA (stream A) is preferably introduced at the side of the separating wall 8, the inflow A being introduced from above onto the partial separating segment 4a, whose upper edge is preferably at least 10% and more preferably at least 20% of the total height of the separating wall 8 below the upper edge of the separating wall 8, and preferably at least 10% and more preferably at least 30% of the total height of the separating wall 8 above the lower edge of the separating wall 8.

It is possible to use any of the evaporators known in the art for this purpose (e.g. the evaporator 3 in FIGS. 1 to 5), suitable examples thus being natural circulation evaporators, forced circulation evaporators or plug-in evaporators. It will be preferable to use horizontal evaporators of the kettle type or vertical falling film evaporators. The same applies to the condensers (e.g., the condenser 2 in FIGS. 1, 3, 4 and 5 or the condensers 2 and 9 in FIG. 2). As the separating wall column 1 is operated under vacuum because of the high boiling point of TDA, condensers with a low pressure loss are recommended. Preferably, the first condenser (e.g., the condenser 2 in FIG. 2) can be integrated into the separating wall column 1 and run as a co-current or counter-current condenser. In this case, other condensers that may be present (e.g., the condenser 9 in FIG. 2) would be arranged next to the separating wall column 1. In another preferred embodiment of the process according to the invention, the condenser (e.g., the condenser 2 in FIGS. 1 to 5) and other condensers that may be present (e.g., the condenser 9 in FIG. 2) are arranged next to the column.

There are no basic restrictions on the separating segments used in the distillation column 1. It is thus possible, for example, to use packings and any types of trays, although bubble-cap trays are preferred and random packings or ordered packings with a low pressure loss are particularly preferred.

The separating wall column 1 used in the practice of the present invention is operated at absolute top pressures of from 30 to 500 mbar and preferably of from 50 to 300 mbar. The corresponding top temperatures are from 100 to 200° C. and preferably from 110 to 190° C., depending on the composition of the inflow. The bottom temperatures are preferably from 170 to 300° C. and more preferably from 180 to 260° C. The inflow temperature is preferably from 130 to 250° C. and more preferably from 150 to 230° C.

Controlling of the separating wall column in the process of the present invention can be difficult under certain circumstances, but the different possible procedures are known in principle. The preferred procedure is to provide a temperature regulator in the upper rectifying section of the separating wall column 1, i.e. above the separating wall 8, the controlled variable for said regulator being the distillate stream, the reflux ratio or, preferably, the amount of reflux J. The bottom product stream P4 can be discharged, e.g., via a flow regulator, which discharges a certain percentage of the column inflow A from the bottom (P4). This is particularly appropriate if the proportion of high boilers in the inflow is known and does not vary too greatly. In this case, it would be possible to use the reflux M as the controlled variable for a level controller in the bottom of the column or in the evaporator. For this purpose, the separating wall column 1 would be extended with a reflux collecting tank located at the side take-off, from which the reflux M is introduced into the stripping section of the main segment. This tank could be equipped with a level controller that acts on the discharged amount of product P3 as the controlled variable. These measures ensure stable operation of the column and hence achieve a further improvement in product purity.

The process according to the invention affords an m-TDA which leads to particularly high yields in phosgenation by the common methods according to the state of the art (e.g., Ullmann's Encyclopedia of Industrial Chemistry, Wiley-VCH, 7th Edition, Release 2005, under the keywords "isocyanates, organic"). This gives an m-TDI having a particularly low coloration and a particularly low yellowing tendency.

The following Examples are given to illustrate the present invention in greater detail.

EXAMPLES

Example 1

6931 kg/h of stream A composed of 39 kg/h of p-TDA, 2.51.8 kg/h of o-TDA, 25.8 kg/h of low boilers and 90.8 kg/h of high boilers, the remainder being m-TDA was introduced into a separating wall column 1. The column was constructed as shown in FIG. 5. The number of theoretical plates in the individual separating segments was 17 for separating segment 4a, 9 for separating segment 5, 17 for separating segment 6, 22 for separating segment 7, and 9 for separating segment 4b. The separating wall column was operated at an absolute top pressure of 90 mbar, measured downstream of the condenser 2. The amount of reflux J was 9210 kg/h and the evaporator 3 had a power of 1446 kW. The ratio of stream E to stream G was adjusted to 0.2:0.8. 1487.8 kg/h were introduced as the stream M into the separating segment 5.

166.5 kg/h of stream P4, containing 45.3 wt. % of m-TDA, the remainder being m-TDA was obtained under these conditions. 6941 kg/h were discharged as the product stream P3, the latter containing 0.59 wt. % of p-TDA and 0.10 wt. % of o-TDA. The product stream P2 was 158.9 kg/h and contained 3.2 wt. % of low boilers and 1.0 wt. % of m-TDA. The stream P1 contained 18 wt. % of low boilers and otherwise essentially o-TDA.

Comparative Example 1

This Example illustrates a process carried out in accordance with the state of the art. The stream A defined in Example 1 was introduced into a conventional isomer separation column. The segment located below the inflow had 17 theoretical separating plates and the segment located above the inflow had 30 theoretical separating plates. The mixture of m-TDA and high boilers discharged from the bottom of the isomer separation column was partially evaporated in a downstream evaporator. The liquid stream discharged from the evaporator was composed of high boilers and m-TDA. The vapor stream obtained from the evaporator was condensed and was composed of the m-TDA free of high boilers.

The isomer separation column was operated at a top pressure of 90 mbar, measured downstream of the condenser. The reflux was 8876 kg/h and the evaporator of the isomer separation column had a power of 1392 kW.

A stream of 199 kg/h, containing 1.0% of m-TDA and 4.3% of low boilers, was discharged as the liquid top product under these conditions. The uncondensed, gaseous top product contained 23% of low boilers. The downstream evaporator and condenser were operated at a pressure of 150 mbar and the temperature in the evaporator outlet was 231° C. 160 kg/h were discharged from the bottom and the m-TDA content of this stream was 49%. The stream withdrawn as product from the condenser was 6497 kg/h and the o-TDA content was 0.1%, the p-TDA content 0.59% and the content of high boilers 0.2%. The evaporator was operated with a heating power of 1039 kW.

The separation of 6931 kg/h of crude TDA carried out according to the state of the art required an energy expenditure of 2431 kW. The process according to the invention required only 1446 kW.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of m-toluenediamine comprising:
   a) hydrogenating dinitrotoluene in the presence of a catalyst,
   b) separating the catalyst, water and optionally solvent from the product of a) to obtain crude toluenediamine, and
   c) distilling the crude toluenediamine in a distillation column having a separating wall to separate the crude toluenediamine into at least four product streams P1, P2, P3 and P4 wherein
      (i) the product stream P1 comprises low boilers,
      (ii) the product stream P2 comprises o-toluenediamine,
      (iii) the product stream P3 comprises m-toluenediamine, and
      (iv) the product stream P4 comprises high boilers and m-toluenediamine.

2. The process of claim 1 in which the crude toluenediamine is introduced into the distillation column in a region near the separating wall.

3. The process of claim 1 in which the crude toluenediamine is introduced into the distillation column from above the separating wall for preliminary separation of the crude toluenediamine.

4. The process of claim 1 in which the crude toluenediamine is introduced into the distillation column at a side of the separating wall.

5. The process of claim 4 in which the crude toluenediamine is introduced into a separating segment of the distillation column with the separating segment having (a) an upper edge which is below the separating wall's upper edge by a distance which is at least 10% of the total height of the separating wall and (b) a lower edge which is above the separating wall's lower edge by a distance which is at least 10% of the total height of the separating wall.

6. The process of claim 1 in which the stream P4 is withdrawn from the distillation column's bottom.

7. The process of claim 1 in which the stream P3 is withdrawn from the distillation column in a region of the separating wall.

8. The process of claim 1 in which the product stream P2 withdrawn from the distillation column as a side stream.

9. The process of claim 1 in which a vapor stream withdrawn from the top of the distillation column is condensed, and one portion of this condensate is withdrawn as the product stream P2 and another portion of this condensate is introduced into the distillation column as reflux.

10. The process of claim 9 in which only a portion of the vapor stream is condensed.

11. The process of claim 1 in which the product stream P4 is withdrawn from the distillation column's bottom and further treated to remove m-toluenediamine.

12. The process of claim 11 in which the m-toluenediamine is removed from stream P4 by evaporation in a kneader dryer.

13. The process of claim 11 in which withdrawn product stream P4 is introduced into a second distillation column at its top and at least a portion of product stream P2 is introduced into the second distillation column at a point below that where the product stream P4 is introduced, and a stream S is withdrawn from the second distillation column and recycled into the distillation column with the separating.

14. A process for the production of m-toluene diisocyanate comprising phosgenating m-toluenediamine prepared by the process of claim 1.

* * * * *